June 8, 1965 F. W. ANDERSON Plant Pat. 2,534
ALMOND TREE
Filed April 13, 1964
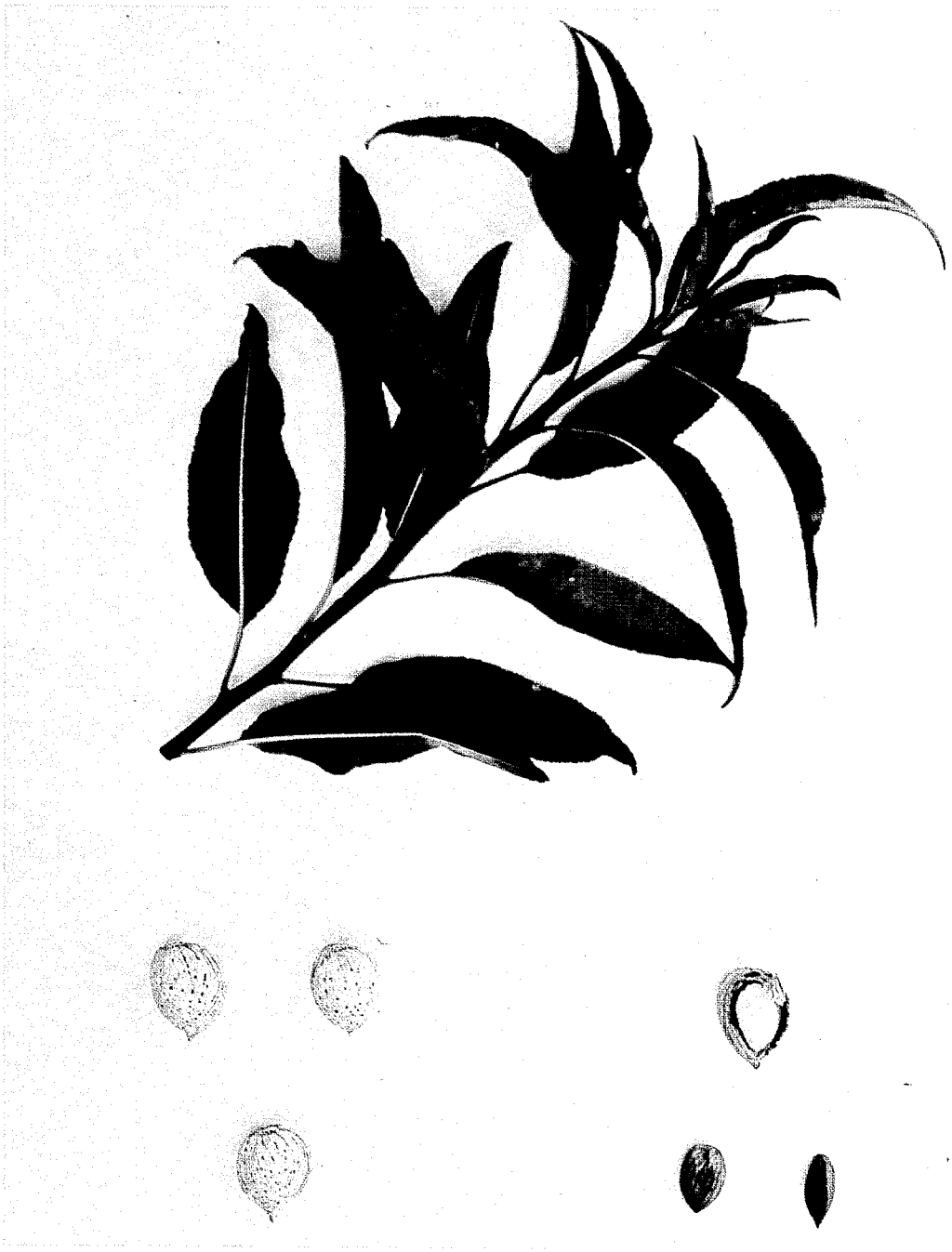
INVENTOR
*Frederic W. Anderson*
*Webster & Webster*
ATTYS.

United States Patent Office

Plant Pat. 2,534
Patented June 8, 1965

2,534
ALMOND TREE

Frederic W. Anderson, Merced, Calif., assignor to Arthur Bright, Le Grand, Calif.

Filed Apr. 13, 1964, Ser. No. 359,536
1 Claim. (Cl. Plt.—30)

This invention relates to a new and distinct variety of almond tree originated by me in my experimental orchard located near Le Grand, Merced County, California, during the course of a long and continuing plant breeding program seeking improved varieties of fruits and nuts, including almonds.

The present variety of almond tree was originated by me in the following manner:

Several thousand seeds were gathered from a row of Mission (unpatented) almond trees growing between adjacent rows of trees of the Nonpareil (unpatented) almond. Thus, such seeds—when planted—produced seedlings of which the seed parent was the Mission, and the pollen parent probably the Nonpareil. These seedlings were maintained under careful observation, and upon bearing nuts, one such seedling (which is the present variety) evidenced certain novel and desirable characteristics for commercial growing.

The variety was, therefore, selected by me for this purpose and I subsequently asexually reproduced it in my experimental orchard, located as aforesaid, by top-working on mature orchard trees. Such asexual reproductions ran true to the parent in all respects.

In comparison to the Nonpareil (long the most important almond grown in California), the herein claimed variety is advantageously distinctive in the following respects:

Firstly, the nuts have a heavier, harder, and better sealed shell which makes the kernels less susceptible to contamination by dust and moisture, and damage by insects, birds, fungi, and other organisms. Further, by reason of such improved shell, the nuts better withstand harvest and hulling by power actuated machines used for knocking, raking, picking up, hulling, and shelling.

Secondly, the nuts weigh approximately ten percent more than the Nonpareil but the kernels average approximately twenty percent smaller in size; such smaller kernals being relatively thin and flat and thus of the type in demand by confectioners for use in candy bars.

Thirdly, the shell is of a uniformly light straw color; such attractive color of the shell, together with a minimum of defective kernels, making the nuts especially desirable for in-shell sales.

The drawing comprises an illustration, by photographic reproduction in color, of a first year shoot with leaves; nuts with the hull removed; a nut with one-half of the shell removed and the kernal cut to expose the meat; a kernel from one side; and another kernal from one edge.

Referring now more specifically to the botanical details of this new and distinct variety of almond tree, the following is an outline description thereof; all major color plate identifications, by comparison with fresh specimens, being by reference to Maerz and Paul Dictionary of Color; except where common terms of color definition are employed:

Tree:
- *Density.*—Dense.
- *Size.*—Large.
- *Vigor.*—Vigorous.

Trunk:
- *Form.*—Stocky.
- *Texture.*—Medium.

Branches:
- *Form.*—Medium.
- *Texture.*—Medium.
- *Branching habit.*—Upright.

Foliage: Quantity—abundant.

Leaves:
- *Size.*—Medium. Average length—4". Average width—15/16".
- *Shape.*—Oval.
- *Thickness.*—Medium.
- *Margin.*—Glandular; crenate.
- *Petiole.*—Medium length; medium thickness.
- *Glands.*—Average number and position—2 on petiole, and 2 on base of blade. Alternate; medium size.
- *Color.*—Top side—medium green (23–J–7). Under side—lighter green (22–J–6).

Bloom:
- *Amount of bloom.*—Heavy.
- *Color.*—White.
- *Blooming period*—Late, approximately with Mission.

Crop:
- *Bearing.*—Regular bearer.
- *Productivity.*—Heavy.
- *Distribution of nuts on tree.*—Well distributed.
- *Harvest period.*—Early to medium; with or a few days after Nonpareil.
- *Tenacity.*—Hangs well on tree; easy to harvest; easy to hull.

Hull:
- *Form.*—Regular.
- *Thickness.*—Thin.
- *Color.*—Gray green.

Nut:
- *Size.*—Medium to small. Average length—1⅛". Average thickness—13/16".
- *Nuts per pound on average sample.*—250–300.
- *Form.*—Length/width—ovate. Width/thickness—medium.
- *Shell.*—Hard; smooth. Outer shell—hard. Inner shell—hard; well sealed.
- *Color.*—Uniformly light straw (11–F–4).
- *Pits.*—Small; numerous.
- *Base.*—Equare.
- *Stem scar.*—Small.
- *Apex.*—Acute.
- *Wing.*—Narrow; thin.
- *Inner surface.*—Light.
- *Ventral streak.*—Light.
- *Percentage of kernel to nut on average sample.*—50 percent.

Kernel:
- Size.—Medium to small. Average length—⅞". Average width—½". Average thickness—5/16".
- *Kernels per ounce on average sample.*—30–35.
- *Form.*—Length/width—ovate. Width/thickness—medium to flat.
- *Base.*—Square.
- *Stem scar.*—Small.
- *Apex.*—Obtuse.
- *Surface.*—Smooth.
- *Pellicle.*—Thin.
- *Pubescence.*—Medium.
- *Color.*—Medium brown (14–I–11).
- *Number of doubles.*—Very few.
- *Defective kernels.*—Very few.
- *Flavor.*—Sweet.
- *Quality.*—Very good.

The tree and its nuts herein described may vary in slight detail due to climatic and soil conditions under which this variety may be grown; the present description being of the variety as grown in the Central Valley of California.

The following is claimed:

A new and distinct variety of almond tree, substantially as illustrated and described, characterized—in comparison to the Nonpareil—by nuts ripening at the same time or a few days later and having a heavier, harder, and better sealed shell; by nuts which weigh approximately ten percent more but whose kernels are approximately twenty percent smaller, relatively thin and flat, and infrequently defective; and by nuts having shells of uniformly light straw color.

No references cited.

ABRAHAM G. STONE, *Primary Examiner.*